United States Patent
Magata et al.

(10) Patent No.: US 6,916,930 B2
(45) Date of Patent: Jul. 12, 2005

(54) RADIOACTIVE IODINE-LABELED COMPOUND

(75) Inventors: Yasuhiro Magata, Hamamatsu (JP); Hideo Saji, Kyoto (JP)

(73) Assignee: Fuji Photo Film Co., Ltd., Kanagawa (JP)

(*) Notice: Subject to any disclaimer, the term of this patent is extended or adjusted under 35 U.S.C. 154(b) by 0 days.

(21) Appl. No.: 10/665,506

(22) Filed: Sep. 22, 2003

(65) Prior Publication Data

US 2004/0228793 A1 Nov. 18, 2004

(30) Foreign Application Priority Data

Mar. 19, 2003 (JP) .................................. 2003-075638

(51) Int. Cl.$^7$ ............................................. C07D 417/14
(52) U.S. Cl. ..................................................... 546/270.1
(58) Field of Search ........................................ 546/270.1

(56) References Cited

PUBLICATIONS

Kawakami et al., "Synthesis and Evaluation of Novel Rhodacyanine, etc.," J. Med. Chem. 1997, 40, 3151–3160.*

* cited by examiner

*Primary Examiner*—Patricia L. Morris
(74) *Attorney, Agent, or Firm*—Sughrue Mion, PLLC

(57) ABSTRACT

A radioactive iodine-labeled compound represented by the following formula

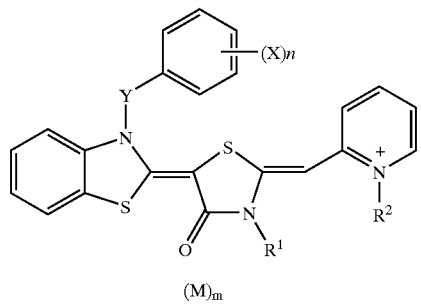

wherein X represents a radioactive iodine atom which may substitute at an arbitrary position on the benzene ring (preferably $^{123}$I, $^{125}$I and the like.), n represents an integer of 1 to 3, $R^1$ and $R^2$ each independently represent a substituted or unsubstituted alkyl group, Y represents an alkylene group having 1 to 6 carbon atoms (preferably methylene group), M represents a counter ion, and m represents the number of ions required to neutralize the charge of the molecule. A radioactive iodine-labeled compound that can selectively accumulate in tumor cells or tumor tissue and a scintillation imaging agent containing the compound are provided.

5 Claims, 1 Drawing Sheet

RADIOACTIVE IODINE-LABELED COMPOUND

FIELD OF THE INVENTION

The present invention relates to a novel radioactive iodine-labeled compound and a scintigraphy imaging agent.

RELATED ART

For therapeutic treatment of a disease, it is important to detect morphological and functional changes in a living body resulting from the disease in an early stage of the disease. In particular, for treatment of cancer, first observation of location and size of a tumor may become highly important means to determine strategy of subsequent therapeutic treatments. Examples of the methods already tried include biopsy by centesis or the like, as well as image diagnostic methods such as X-ray imaging, MRI imaging and ultrasonography. Although biopsy is effective for definite diagnosis, it imposes much stress on subjects to be examined, and is not suitable for longitudinal observation of changes in lesions.

As one of noninvasive image diagnostic methods utilizing a physiological function of a pathological site, a method is known in which imaging by a radionuclide procedure is carried out by using a compound containing a radioactive isotope as a scintigraphy imaging agent. Scintigraphy imaging is considered to be breakthrough, overcoming the limits of conventional tumor diagnostic methods such as image diagnosis by morphological visualization (CT, MRI, ultrasonography), and promising means for examination of microcarcinoma or systemic carcinoma and detection of recurrent carcinoma.

A scintigraphy imaging agent is required to have an ability to distinguish a normal site from a tumor site and to selectively accumulate in a tumor site. Examples of compounds having such accumulating property in tumor include, for example, porphyrin compounds such as hematoporphyrin used in the photodynamic therapy (PDT) (photophyrin, benzoporphyrin and the like are also included in this group of compounds, see, Lipspn R. L. et al., ibid.; Meng T. S. et al., SPIE (1992) 1641, 90–98; WO84/04665 and the like). However, since these compounds are originally used in PDT, they have phototoxicity (this property is required for PDT), and hence they are not desirable as diagnostic agents. Moreover, tumor selectivity of these compounds is not sufficient.

As one of the tumor targeting methods, a method of therapeutic treatment of hepatic cancer is also known in which lipiodol as an oily imaging agent having high tumor selectivity is used as a base material, and a synthetic polymeric antitumor agent (antitumor agent obtained by reacting monobasic acid anhydride of styrene maleic acid with a proteinous antitumor agent, neocarzinostatin) is dissolved in the base material and then the solution is injected into hepatic artery (Maeda et al., Gan to Kagakuryoho (Cancer and Chemotherapy), vol. 12, 3, PART II, 773–781, March 1985). Further, Rhodamine 123, a lipid-soluble cation compound, was found to have accumulating property in tumor (Proc. Natl. Acad. Sci. U.S.A., 79, 5292–5296 (1982)), and this property was reported to be derived from a difference in mitochondrial membrane electric potential between normal cells and tumor cells (J. Biol. Chem., 260, 13844–13850 (1985)). Rhodamine 123 is a monovalent cation compound having high lipid-solubility due to delocalization of π electrons. A class of compounds that selectively accumulate in tumor by utilizing an electric potential difference caused by decrease of electric potential of the mitochondrial inner membrane in tumor cells are generically called as DLC (π-electron delocalized lipophilic cations).

Cyanine compounds and rhodacyanine compounds, which are spectral sensitization pigments or dyes used in the field of photographic science, are also lipid-soluble monovalent cation compounds similar to Rhodamine 123, and several compounds having the property of accumulating in tumor have been reported (as a typical compound, for example, MKT077: 1-ethyl-2-[[3-ethyl-5-(3-methylbenzothiazolin-2-yliden)-4-oxothiazolidin-2-ylidene]methyl]pyridinium chloride is described in J. Med. Chem., 40, 3151–3160 (1997)). For example, WO00/16810 discloses a method of using a cyanine compound, that emits fluorescence in a near-infrared region having excellent tissue permeability in vivo, as a fluorescence imaging agent by accumulation in a tumor, and Japanese Patent No. 2864188 discloses utilization of a rhodacyanine compound as an antitumor agent. However, these patent documents relates to an object of increasing water solubility of the compounds for the application as antitumor agents, and therefore, the compounds fail to have sufficient accumulating property in tumor. No method is known so far in which cationic compounds having high accumulating property in tumor, in particular, cyanine and rhodacyanine dye compounds, are labeled with radioactive iodine nuclear species.

DISCLOSURE OF THE INVENTION

An object of the present invention is to provide a scintillation imaging agent which enables specific imaging of tumor. In order to achieve the aforementioned object, the inventors of the present invention utilized the basic structure of MKT077 conventionally known as DLC, and conducted various researches on modification methods for introducing a radioactive iodine atom into the basic structure without degrading the tumor accumulating property of the compound. As a result, they found that the compounds represented by the following formula (I) had highly potent property of accumulation in tumor cells, and accordingly, they had a superior property as scintillation imaging agents. The present invention was achieved on the basis of the above findings.

The present invention thus provides radioactive iodine-labeled compounds represented by the following formula (I):

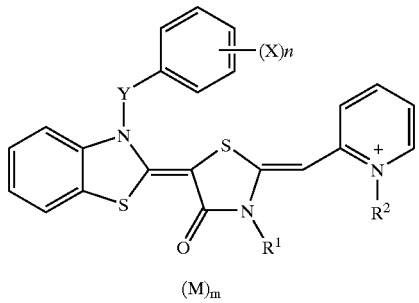

wherein X represents a radioactive iodine atom which may substitute at any position on the benzene ring, n represents an integer of 1 to 3, $R^1$ and $R^2$ each independently represent a substituted or unsubstituted alkyl group, Y represents an alkylene group having 1 to 6 carbon atoms, M represents a counter ion, and m represents the number of ions required to neutralize the charge of the molecule.

According to preferred embodiments of the present invention, provided are the aforementioned radioactive iodine-labeled compounds, wherein X is $^{123}$I or $^{125}$I; the aforementioned radioactive iodine-labeled compounds, wherein $R^1$ and $R^2$ each independently represent an unsubstituted alkyl group having 4 or less carbon atoms; and the aforementioned radioactive iodine-labeled compounds, wherein Y represents methylene group. As a particularly preferred compound, the following radioactive iodine-labeled compound is provided.

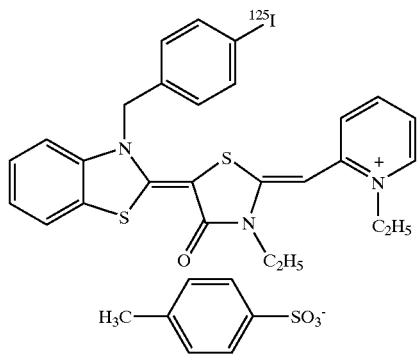

From another aspect, the present invention also provides scintigraphy imaging agents, which comprise the aforementioned radioactive iodine-labeled compounds and are used for imaging of a tumor site. According to a preferred embodiment of this aspect of the present invention, provided is the aforementioned scintigraphy imaging agents, which are used for imaging of tumor cells or tumor tissue. Further, the present invention also provides use of the aforementioned radioactive iodine-labeled compounds for manufacture of the aforementioned scintigraphy imaging agents; methods for scintigraphy imaging, which comprise the step of administering a scintigraphy imaging agent containing the aforementioned radioactive iodine-labeled compound to a mammal including human and then detecting radiation emitted from the radioactive iodine-labeled compound; and methods for imaging of tumor cells or tumor tissue, which comprises the step of administering a scintigraphy imaging agent containing the aforementioned radioactive iodine-labeled compound to a mammal including human and then detecting radiation emitted from the radioactive iodine-labeled compound.

BEST MODE FOR CARRYING OUT THE INVENTION

Figure 1:
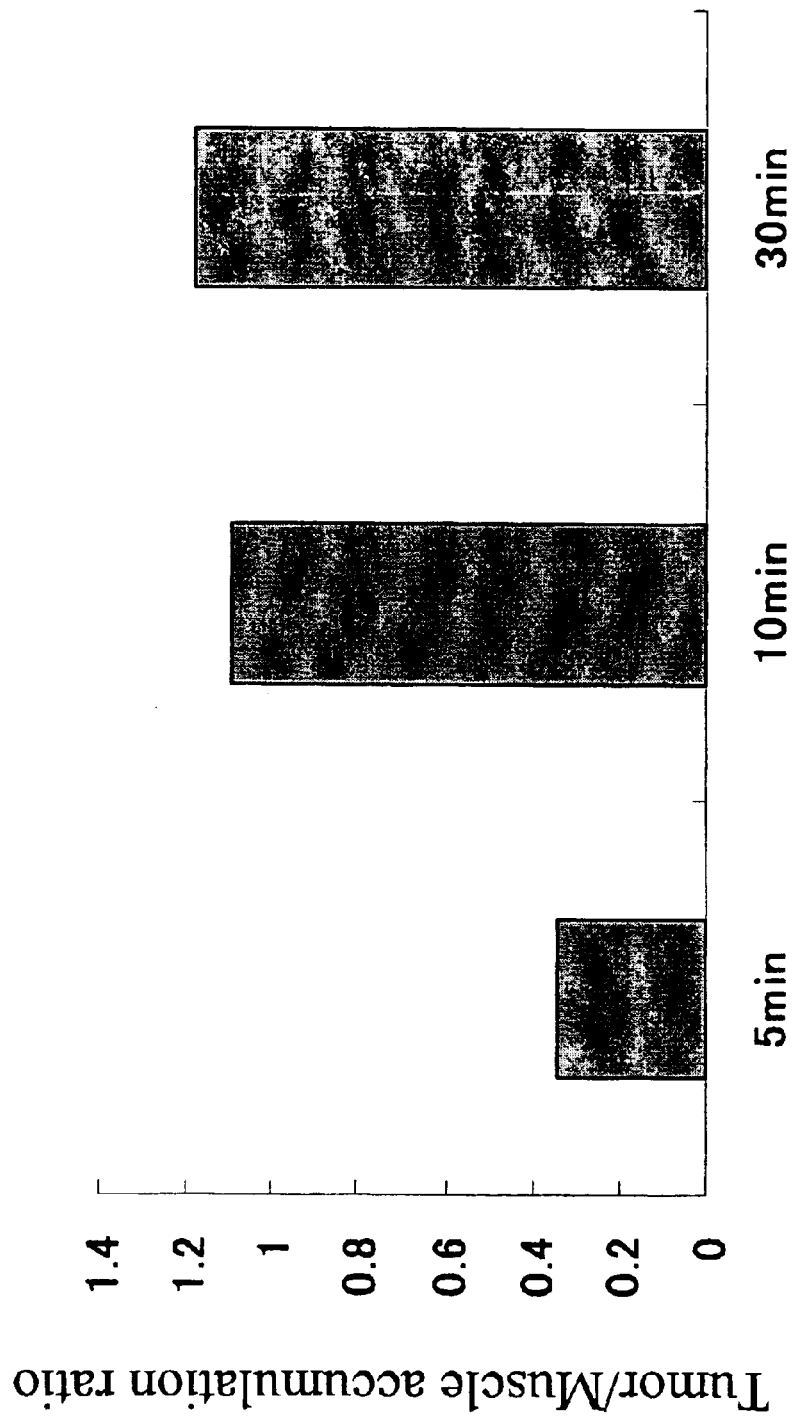
FIG. 1 shows ratios of accumulation of the compound of the present invention in tumor tissue and muscle tissue of a nude mouse.

X represents a radioactive iodine atom, which may substitute at an arbitrary position on the benzene ring. Types of the radioactive isotope of iodine atom are not particularly limited. Preferred examples include $^{122}$I, $^{123}$I, $^{125}$I, or $^{131}$I. $^{123}$I and $^{125}$I are more preferred. Substituting positions and numbers (n) of X on the benzene ring are not particularly limited. The compounds having two radioactive iodine atoms at the 2- and 4-positions of the benzene ring are preferred, and the compounds having one radioactive iodine atom at the 4-position of the benzene ring is more preferred.

$R^1$ and $R^2$ each independently represent a substituted or unsubstituted alkyl group. In the specification, the alkyl group may be straight, branched, or cyclic, or a combination thereof. The cyclic alkyl group includes a polycyclic alkyl group such as a bicycloalkyl group, and also includes a so-called steroid structure having cyclopentanohydrophenanthrene structure. Alkyl moieties of other substituents containing the alkyl moiety have the same meaning. The types, number and substituting positions of substituents on the alkyl group are not particularly limited. Examples of the substituents on the alkyl group include a halogen atom (fluorine, chlorine, bromine or iodine), an alkenyl group (including a cycloalkenyl group and a bicycloalkenyl group), an alkynyl group, an aryl group, a heterocyclic group, cyano group, hydroxyl group, nitro group, carboxyl group, an alkoxy group, an aryloxy group, silyloxy group, a heterocyclyloxy group, an acyloxy group, carbamoyloxy group, an alkoxycarbonyloxy group, an aryloxycarbonyloxy group, an amino group (including anilino group), an acylamino group, aminocarbonylamino group, an alkoxycarbonylamino group, an aryloxycarbonylamino group, sulfamoylamino group, an alkyl or arylsulfonylamino group, mercapto group, an alkylthio group, an arylthio group, a heterocyclylthio group, sulfamoyl group, sulfo group, an alkyl or arylsulfinyl group, an alkyl or arylsulfonyl group, an acyl group, an aryloxycarbonyl group, an alkoxycarbonyl group, carbamoyl group, an aryl or heterocyclylazo group, imido group, phosphino group, phosphinyl group, phosphinyloxy group, phosphinylamino group, silyl group and the like. As $R^1$ and $R^2$, an unsubstituted alkyl group having 4 or less carbon atoms can be preferably used, and it is more preferred that $R^1$ and $R^2$ both represent ethyl group.

Y represents an alkylene group having 1 to 6 carbon atoms. The alkylene group may be straight or branched, and may be substituted. When the alkylene group has a substituent, the substituents explained for the alkyl group can be used as the substituent. An unsubstituted alkylene group is preferably used. The number of carbon atoms in the alkylene group is preferably 1 to 3, more preferably 1 or 2. The most preferred alkylene group is methylene group.

M represents a counter ion. M may be a cation or an anion. Examples of the cation include an alkali metal ion such as sodium ion, potassium ion and lithium ion and an organic ion such as tetraalkylammonium ion and pyridinium ion. The anion may be an inorganic anion or an organic anion, and examples thereof include a halogen anion (for example, fluoride ion, chloride ion, bromide ion, iodide ion and the like), a substituted arylsulfonate ion (for example, p-toluenesulfonate ion, p-chlorobenzenesulfonate ion and the like.), an aryldisulfonate ion (for example, 1,3-benzenedisulfonate ion, 1,5-naphthalenedisulfonate ion), an alkylsulfate ion (for example, methylsulfate ion and the like.), sulfate ion, thiocyanate ion, perchloride ion, tetrafluoroborate ion, picrate ion, acetate ion, trifluoromethanesulfonate ion and the like. Further, M may be a hydrogen ion. M is preferably an anion. The anion is preferably a halogen anion, a substituted arylsulfonate ion or acetate ion, more preferably chloride ion or p-toluenesulfonate ion.

Specific examples of the compound of the present invention will be mentioned below. However, the scope of the present invention is not limited to these examples. Compounds wherein Y is methylene group will be mentioned as preferred embodiments of the present invention.

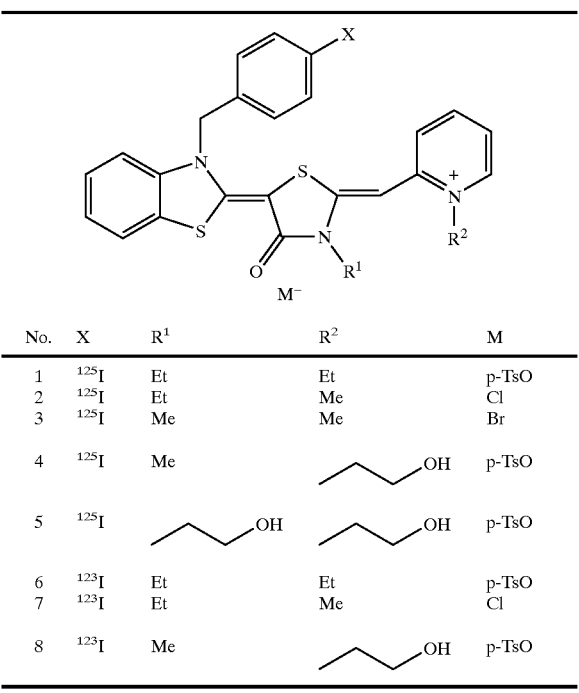

| No. | X | R¹ | R² | M |
|-----|------|------|---------|-------|
| 1 | ¹²⁵I | Et | Et | p-TsO |
| 2 | ¹²⁵I | Et | Me | Cl |
| 3 | ¹²⁵I | Me | Me | Br |
| 4 | ¹²⁵I | Me | ⁀⁀OH | p-TsO |
| 5 | ¹²⁵I | ⁀⁀OH | ⁀⁀OH | p-TsO |
| 6 | ¹²³I | Et | Et | p-TsO |
| 7 | ¹²³I | Et | Me | Cl |
| 8 | ¹²³I | Me | ⁀⁀OH | p-TsO |

The compounds of the present invention may have 1 or more asymmetric centers. As for such compounds, stereoisomers such as optically active substances or diastereoisomers based on the asymmetric centers exist. Any stereoisomers in pure forms, any mixtures of stereoisomers, racemates and the like all fall within the scope of the present invention. Further, the compounds of the present invention may form a hydrate or a solvate, and these substances also fall within the scope of the present invention.

Methods for producing the compounds of the present invention are not particularly limited, and the compounds of the present invention can be produced by any appropriate method. In general, preparation of a radioactive iodine compound can be carried out by synthesizing a corresponding non-radioactive iodine compound and then employing a known method described in Appl. Radiat. Isot., 37(8), 907 (1986) or the like. A method for producing typical compounds of the present invention will be specifically described in detail in the scheme and the example described below. Therefore, those skilled in the art can readily produce any compounds represented by the formula (I) by referring to this production method and suitably choosing starting compounds, reagents, reaction conditions and the like, and by suitably modifying or changing the method as required.

For example, it would be easily understood by those skilled in the art that the reaction similarly proceeds when an appropriate alkyliodobenzene derivative is used instead of the starting material 1C, and that a functional group such as bromine atom or tosyl group as a leaving group can be appropriately introduced at any position of the alkyl group in the alkyliodobenzene derivative. The alkyl group of the alkyliodobenzene derivative can be converted to an alkyl group having an appropriate length from an easily available starting compound, for example, by the Wittig reaction, Barbier-Wieland decomposition, Arndt-Eistert synthesis, a method of using acetylide (for example, according to the method described in Tetrahedron Lett. 35, 9501 (1994)), a method of using chloroformic acid ester (described in, for example, Synthesis 427 (1986)), a method of using diethyl malonate (described in, for example, Arch. Pharm. (Weinheim) 328, 271 (1995)) or the like. Further, the iodine atom on the benzene ring of the alkyliodobenzene derivative can be introduced by using a benzene derivative as a starting material, for example, according to the method described in Richard C. Larock, Comprehensive Organic Transformations (VCH).

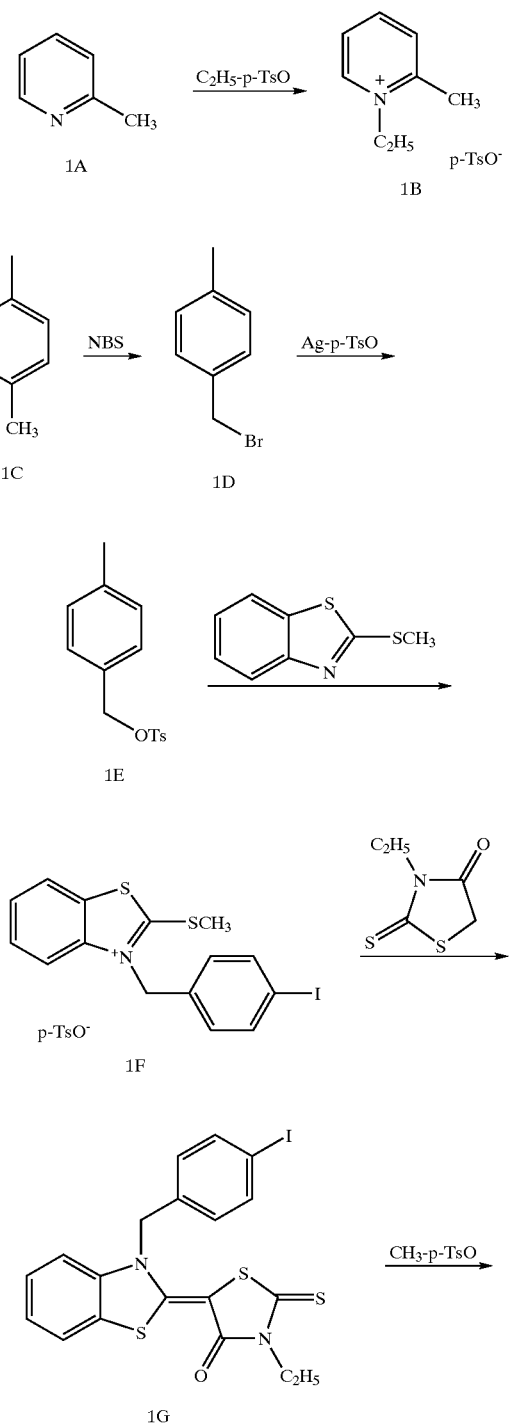

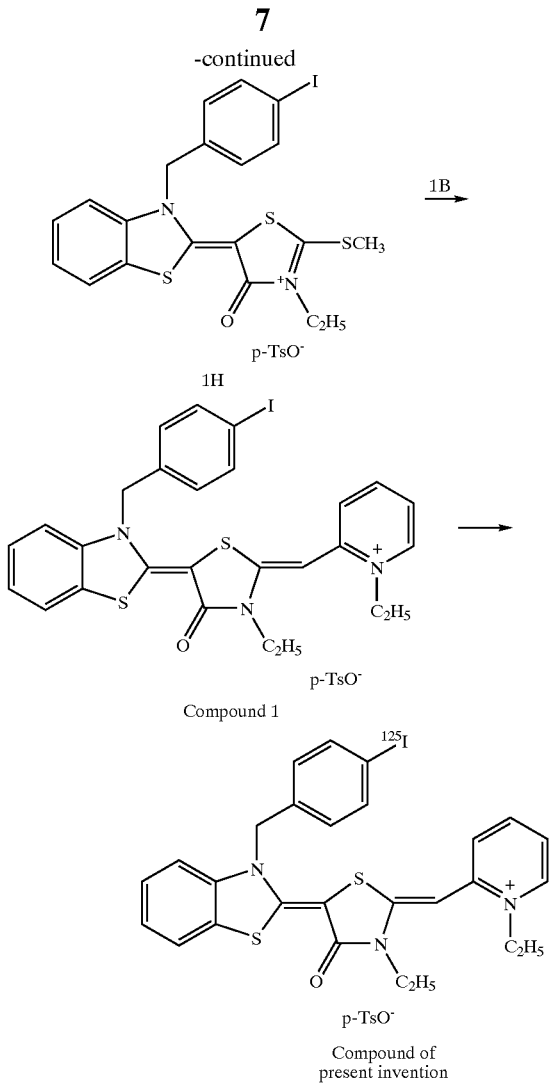

Compound 1

Compound of present invention

The compounds represented by the aforementioned formula (I) have a property of accumulating in tumor cells, and scintigraphy imaging agents containing the compounds as an active ingredient can selectively image a tumor cell or tumor tissue. Although it is not intended to be bound by any specific theory, the electric potential of mitochondria inner membrane is generally lower in tumor cells than in normal cells, and the compounds of the present invention have a property of selectively accumulating in tumor cells based on this electric potential difference. The imaging agent of the present invention can be preferably administered parenterally, more preferably intravenously. The agent may sometimes be orally administered. In general, the imaging agent of the present invention can be provided as an injection, preferably an injection for intravenous administration, in the same manner as scintigraphy imaging agents conventionally used in this field. The injection may be provided as a lyophilized powder composition, which is dissolved in water or other suitable medium (for example, physiological saline, glucose infusion, buffer and the like) upon use. A dose of the imaging agent of the present invention is not particularly limited, and the dose may be selected depending on a type of tumor cells or tumor tissue to be imaged, a size of a lesion, age and body weight of a patient and the like, so that radiation emitted in a lesion can be detected from outside of a body.

EXAMPLES

The present invention will be explained more specifically with reference to the following examples. However, the scope of the present invention is not limited to these examples. The compound numbers used in the following examples correspond to the compound numbers used in the above scheme.

Example 1

Synthesis of the Compound of the Present Invention (1) Synthesis of Compound 1B

2-Picoline (Compound 1A, 0.46 g) and ethyl paratoluenesulfonate (1.00 g) were reacted at 140° C. for 2.5 hours. The reaction mixture was cooled to 90° C., then added with acetone (2 ml), and further cooled to room temperature. The produced white precipitates were collected by suction filtration and recrystallized from acetone to obtain Compound 1B (yield: 53.9%). Compound 1B was used in the subsequent reaction without purification.

(2) Synthesis of Compound 1D p-Iodotoluene (Compound 1C, 25 g), N-bromosuccinimide (23.5 g) and benzoyl peroxide (375 mg) were added to carbon tetrachloride (375 ml) and refluxed with heating for 7 hours under photoirradiation. Further, the reaction mixture was stirred overnight at room temperature, then insoluble matters were removed by filtration, and the filtrate was concentrated under reduced pressure. The concentrated residue was recrystallized from ethyl acetate and hexane to obtain Compound 1D (yield: 60.3%).

NMR chemical shift, CDCl$_3$, TMS as standard

δ 7.72 (d, 2H), 7.14 (d, 2H), 4.39 (s, 2H)

(3) Synthesis of Compound 1E

Compound 1D (6.14 g) and silver tosylate (6.08 g) were dissolved in dehydrated acetonitrile (300 ml) and stirred at 50° C. for 5 hours. The precipitated silver bromide was removed by filtration, the filtrate was concentrated under reduced pressure, and the residue was extracted with ether. The ether layer was concentrated under reduced pressure, and then the residue was recrystallized from ether to obtain Compound 1E (yield: 40.8%).

NMR chemical shift, CDCl$_3$, TMS as standard

δ 7.75 (d, 2H), 7.51 (d, 2H), 7.35 (d, 2H), 7.15 (d, 2H), 5.08 (s, 2H), 2.30 (s, 3H)

(4) Synthesis of Compound 1G

Compound 1E (1.00 g), 2-methylthiobenzothiazole (0.311 g) and anisole (0.435 ml) were stirred at 135° C. for 4 hours (production of Compound 1F). The reaction mixture was cooled to room temperature and then added with 3-ethylrhodamine (0.277 g) and acetonitrile (6.2 ml), added dropwise with triethylamine (0.28 g) while the reaction mixture was maintained at 15° C., and stirred at 10° C. for 4 hours. The yellow crystals precipitated in the reaction mixture were collected by suction filtration and washed with acetonitrile and methanol. The obtained crude crystals were suspended in acetone (300 ml), refluxed with heating for 15 minutes and subjected to filtration while the reaction mixture was still hot. Further, the crystals were washed with methanol to obtain Compound 1G (yield: 65%).

NMR chemical shift, CDCl$_3$, TMS as standard

δ 7.93 (d, 1H), 7.78 (d, 1H), 7.66 (d, 2H), 7.52 (t, 1H), 7.35 (t, 1H), 7.14 (d, 2H), 4.83 (s, 2H), 4.10 (q, 2H), 1.20 (s, 3H)

(5) Synthesis of Compound 1H

Compound 1G (1.00 g) and methyl paratoluenesulfonate (2.24 g) were added to N,N-dimethylformamide (1 ml) and stirred at 140° C. for 2.5 hours. The reaction mixture was cooled to 95° C., then added with acetone (8.8 ml) and stirred with cooling to 10° C. The precipitated yellow crystals were collected by filtration and then washed with acetone with heating for 15 minutes to obtain Compound 1H (yield: 64.2%).

NMR chemical shift, $CDCl_3$, TMS as standard

δ 8.18 (d, 1H), 8.00 (d, 1H), 7.70 (dd, 1H), 7.66 (d, 2H), 7.52 (dd, 1H),7.46 (d, 2H), 7.14 (d, 2H), 7.10 (d, 2H), 4.83 (s, 2H), 4.17 (q, 2H), 3.05 (s, 3H), 2.27 (s, 3H), 1.33 (t, 3H)

(6) Synthesis of Compound 1

Compound 1H (1.00 g) and Compound 1B (0.429 g) were added to acetonitrile (7.3 ml), heated to 70° C. and added with triethylamine (0.443 g), and the reaction mixture was stirred for 1.5 hours at the same temperature. The reaction mixture was added dropwise with ethyl acetate (7.3 ml) and cooled to 30° C., and the produced crystals were collected by filtration. The crude crystals were dissolved in methanol (4.7 ml), added with ethyl acetate (14.6 ml), stirred at 50° C. for 3 hours, and then cooled to room temperature. The orange color crystals were collected by filtration. Further, the crystals were dissolved in methanol (1 ml), and the solution was centrifuged at 3000 rpm for 10 minutes. The supernatant was concentrated under reduced pressure to obtain Compound 1 (yield: 32.1%).

Melting point: 268–270° C.

λmax (MeOH) [nm](e): 494 ($4.82 \times 10^4$)

NMR chemical shift, $CDCl_3$, TMS as standard

δ 8.70 (d, J=8.0 Hz, 1H), 8.26 (t, J=8.0 Hz, 1H), 8.06 (d, J=8.0 Hz,1H), 7.88 (dd, J=8.0, 8.0 Hz, 1H), 7.66 (d, J=8.9 Hz, 2H), 7.61 (dd, J=8.0, 8.0 Hz, 1H), 7.49 (d, J=8.9 Hz, 2H), 7.47 (dd, J=8.0, 8.0 Hz, 1H), 7.28 (dd, J=8.0, 8.0 Hz, 1H), 7.14 (d, J=8.9 Hz, 2H), 7.11 (d, J=8.9 Hz, 2H), 5.98 (s, 3H), 4.83 (s, 2H), 4.60 (q, J=7.2 Hz, 2H), 4.11 (q, J=7.2 Hz, 2H), 2.28 (s, 3H), 1.43 (t, J=7.2 Hz, 3H), 1.24 (t, J=7.2 Hz, 3H)

(7) Synthesis of the Compound of the Present Invention

Compound 1 was added to 0.1 M aqueous sodium hydroxide and extracted with ethyl acetate. The organic layer was concentrated under reduced pressure. The concentrate (0.1 mg) was dissolved in methanol (100 μl), added with 4 mM aqueous copper sulfate (5.0 μl), 0.15 M aqueous ammonium sulfate (2.0 μl) and $^{125}$I-NaI alkaline solution, and a reaction was allowed at 120° C. in a closed system on an oil bath for 6 hours. The compound of the present invention was separated from the reaction mixture by HPLC with the following conditions.

Column: Chemco Lichrosorb, 7.5×300 mm
Detection wavelength: 254 nm
Flow rate: 3.0 ml/min
Column temperature: 30° C.
Elution solution: methanol:water=7:3
Yield: 50%
Radiochemical purity: >95%

Example 2

Property of Accumulation in Tumor Cells (1) Media Used (i) LS180 (Human Colon Cancer Cell), SHIN-III (Human Ovary Cancer Cell) and U87MG (Glioma)

A commercially available medium, RPMI1640 (Nissui, 5.1 g), was dissolved in extra pure water (500 ml), autoclaved, and added with L-glutamine (0.15 g), Meylon (7% aqueous sodium hydrogencarbonate, a pharmaceutical preparation for injection, 14 ml) and FBS (55 ml) in a clean bench to prepare a medium. Cells were cultured in this medium.

(ii) NIH3T3 (Fibroblast, Control)

A commercially available DMEM medium (Nissui) was dissolved in extra pure water (500 ml), autoclaved, and added with L-glutamine (0.15 g), Meylon (7% aqueous sodium hydrogencarbonate, a pharmaceutical preparation for injection, 14 ml) and FBS (55 ml) in a clean bench to prepare a medium. Cells were cultured in this medium.

(2) Culture Method (a) Thawing of Cryopreserved Cells

Cells cryopreserved in a medium containing 10% DMSO were thawed, transferred to a 15-ml Falcon tube, and added with PBS to a volume of 5 ml. The mixture was centrifuged at 1300 rpm for 5 minutes. The supernatant was removed by suction, and the precipitates were suspended in PBS (5 ml). The suspension was centrifuged again at 1300 rpm for 5 minutes. The supernatant was removed by suction, and the precipitates were suspended in a medium (10 ml), inoculated in a 10-cm dish and left standing at 37° C. in a 5% $CO_2$ incubator.

(b) Time of Subculture (i) LS180, SHIN-III and U87MG

After 3 days, when the cells were proliferated to 80 to 90% of the 10-cm dish, the cells were subcultured in a 15-cm dish.

(ii) NIH3T3

After 1 week, when the cells were proliferated to 80 to 90% of the 10-cm dish, the cells were subcultured in a 15-cm dish.

(c) Subculture

The 10-cm dish was taken out from the incubator, and the supernatant was removed by suction. The cells were washed three times with PBS, added with trypsin-EDTA (0.05% trypsin, 0.53 mM EDTA tetrasodium salt, 1 ml) and PBS (1 ml) and left standing in a $CO_2$ incubator for 10 minutes. The dish was taken out from the incubator, and separation of the cells was observed. Then, the cells were transferred to a 15-ml Falcon tube. The cells were added with PBS to a volume of 5 ml and centrifuged at 1300 rpm for 5 minutes, and the supernatant was removed by suction. The precipitates were suspended in PBS (5 ml) and centrifuged at 1300 rpm for 5 minutes, and the supernatant was removed by suction. The precipitates were suspended in a medium (8 ml), and inoculated in a volume of 4 ml each to two of 15-cm dishes, to which the medium (16 ml) was added beforehand, and left standing at 37° C. in a 5% $CO_2$ incubator.

(d) Storage

When the cells proliferated to 80 to 90% of the 15-cm dish after 3 days for LS180, SHIN-III and U87MG or after 1 week for NIH3T3, the dish was taken out from the incubator, and the supernatant was removed by suction. The cells were washed three times with PBS, added with trypsin-EDTA (3 ml) and PBS (3 ml) and left standing in a $CO_2$ incubator for 10 minutes. The dish was taken out from the incubator, and separation of the cells was observed. Then, the cells were transferred to a 50-ml Falcon tube. The cells were added with PBS to a volume of 15 ml and centrifuged at 1300 rpm for 5 minutes, and the supernatant was removed by suction. The precipitates were suspended in PBS (15 ml), and the suspension was centrifuged again at 1300 rpm for 5 minutes. The supernatant was removed by suction, and the precipitates were suspended in a medium containing 10% DMSO (8 ml). The suspension was divided into four aliquots of 2-ml cryogenic tubes and stored at −80° C. in a deep freezer.

(e) Uptake Experiment

Two days before the uptake experiment, the cells were inoculated on a 24-well plate (500 ml of cell-suspended medium/well, 5 wells/plate per one type of cell). A medium (500 ml) containing the compound (0.5 μCi) obtained in Example 1 was substituted for the medium in 4 wells of the 5 wells in which the cells were inoculated, and incubation was performed. After an uptake time (30 minutes, 1 hour, 3 hours), the supernatant was removed by suction for all of the wells. For the 4 wells to which the compound of the present invention was added, the cells were separated with 0.2 N NaOH and subjected to measurement of radioactivity. For the remaining 1 well, trypsin-EDTA was added to separate the cells, and the number of cells was counted by using a blood cell counter. Percent doses, which were converted to values for 100,000 cells based on the number of cells and radioactivity, and ratios relative to the normal cells (NIH3T3) were calculated. The results are shown in Table 1. As shown from the results in Table 1, the compound of the present invention gave about three times as much uptake in LS180 (human colon cancer cells), about seven times as much uptake in SHIN-III (human ovary cancer cell) and about 7 times as much uptake in U87MG (glioma) as in the normal cells.

TABLE 1

|  | After 30 minutes | After 1 hour | After 3 hours |
| --- | --- | --- | --- |
| LS180 | 3.37 ± 0.31 | 5.33 ± 0.43 | 10.2 ± 0.97 |
| SHIN-III | 6.26 ± 0.73 | 11.7 ± 1.16 | 25.2 ± 2.42 |
| U87MG | 3.19 ± 1.86 | 3.07 ± 0.09 | 5.32 ± 0.70 |
| NIH3T3(control) | 1.40 ± 0.03 | 2.12 ± 0.14 | 3.34 ± 0.18 |

Values are means ± S.D. as % dose/100000 cells

Example 3

Distribution Experiment In Vivo $1.0 \times 10^6$ cells of SHIN-III human ovary cancer cells were subcutaneously inoculated in the femoral region of nude mice (male, 5-week old). After 17 days, the compound of the present invention (18.5 kBq) was dissolved in physiological saline (100 μl) containing 5% DMSO and administered to the mice from the caudal vein. After 5 minutes, 10 minutes and 30 minutes, the mice were sacrificed, and the weight and radioactivity of each organ were measured. The accumulation ratios in the tumor tissue and muscle tissue are shown in FIG. 1. As clearly shown in FIG. 1, the compound of the present invention was demonstrated to accumulate in a higher concentration in the tumor tissue than in the muscle in the in vivo system using nude mice transplanted with SHIN-III.

The compounds of the present invention thus have superior property of accumulation in a tumor, and are useful for diagnosis of tumor as radioactive iodine-labeled scintigraphy imaging agents.

What is claimed is:

1. A radioactive iodine-labeled compound represented by the following formula (I):

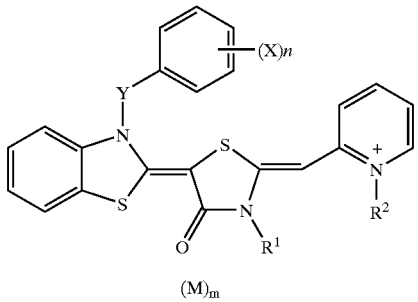

wherein X represents a radioactive iodine atom which may substitute at an arbitrary position on the benzene ring, n represents an integer of 1 to 3, $R^1$ and $R^2$ each independently represent a substituted or unsubstituted alkyl group, Y represents an alkylene group having 1 to 6 carbon atoms, M represents a counter ion, and m represents the number of ions required to neutralize the charge of the molecule.

2. The compound according to claim 1, wherein X is $^{123}$I or $^{125}$I.

3. The compound according to claim 1, wherein $R^1$ and $R^2$ each represent an unsubstituted alkyl group having 4 or less carbon atoms.

4. The compound according to claim 1, wherein Y represents methylene group.

5. A radioactive iodine-labeled compound represented by the following formula

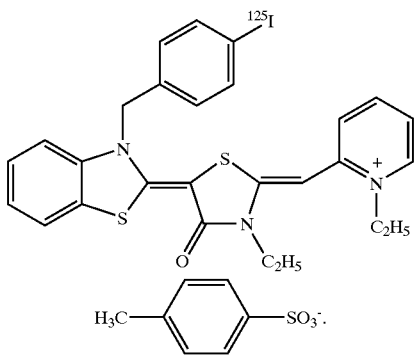

* * * * *